US008560079B2

(12) United States Patent  
Capcelea et al.

(10) Patent No.: US 8,560,079 B2  
(45) Date of Patent: Oct. 15, 2013

(54) BRAZE JOIN

(75) Inventors: Edmond D. Capcelea, Bond Junction (AU); Charles R. A. Leigh, East Ryde (AU)

(73) Assignee: Cochlear Limited, Macquarie University, NSW (AU)

( * ) Notice: Subject to any disclaimer, the term of this patent is extended or adjusted under 35 U.S.C. 154(b) by 1195 days.

(21) Appl. No.: 12/158,915

(22) PCT Filed: Dec. 22, 2006

(86) PCT No.: PCT/AU2006/002012  
§ 371 (c)(1), (2), (4) Date: Feb. 5, 2009

(87) PCT Pub. No.: WO2007/070989  
PCT Pub. Date: Jun. 28, 2007

(65) Prior Publication Data  
US 2009/0292337 A1   Nov. 26, 2009

(30) Foreign Application Priority Data  
Dec. 23, 2005   (AU) .............................. 2005907265

(51) Int. Cl.  
*A61N 1/02* (2006.01)

(52) U.S. Cl.  
USPC .......................................................... 607/57

(58) Field of Classification Search  
USPC .......................................................... 607/57  
See application file for complete search history.

(56) References Cited

U.S. PATENT DOCUMENTS

| 4,509,880 | A | 4/1985 | Wamstad |
| 5,046,242 | A | 9/1991 | Kuzma et al. |
| 5,071,174 | A | 12/1991 | Griffin et al. |
| 5,267,684 | A | 12/1993 | Catheline et al. |
| 5,272,283 | A | 12/1993 | Kuzma |
| 5,430,254 | A | 7/1995 | Loeb et al. |
| 6,276,447 | B1 | 8/2001 | Iguchi et al. |
| 6,586,675 | B1 | 7/2003 | Bealka et al. |
| 7,182,640 | B2 | 2/2007 | Garrett et al. |
| 7,396,265 | B2 | 7/2008 | Darley et al. |
| 2006/0141861 | A1 | 6/2006 | Darley et al. |
| 2006/0175071 | A1 | 8/2006 | Knappen et al. |
| 2008/0060844 | A1 | 3/2008 | Teske et al. |
| 2008/0188707 | A1 | 8/2008 | Bernard et al. |

(Continued)

FOREIGN PATENT DOCUMENTS

| EP | 1484085 | 12/2004 |
| EP | 1820534 | 8/2007 |

(Continued)

OTHER PUBLICATIONS

International Search Report. PCT/AU2006/002012. Mar. 7, 2007.

*Primary Examiner* — Joseph Dietrich  
(74) *Attorney, Agent, or Firm* — Kilpatrick, Townsend & Stockton, LLP

(57) ABSTRACT

A method of forming a braze join between two components is disclosed, in which braze material is introduced into a gap between the two components by capillary action. This assists in reducing flooding. Also disclosed is a component for use with the method, and an assembly produced by the method. In one form, the component comprises a recess or reservoir for storing braze material, in fluid communication with an aperture to allow the braze material to be drawn into the gap by capillary forces. The method may be used in a number of applications including medical devices and more specifically, a cochlear implant.

28 Claims, 7 Drawing Sheets

(56) References Cited

U.S. PATENT DOCUMENTS

| | | |
|---|---|---|
| 2008/0208289 A1 | 8/2008 | Darley et al. |
| 2008/0209723 A1 | 9/2008 | Darley et al. |
| 2008/0290141 A1* | 11/2008 | Shaw et al. .................. 228/155 |
| 2011/0059331 A1 | 3/2011 | Smith et al. |

FOREIGN PATENT DOCUMENTS

| | | |
|---|---|---|
| WO | 0204840 | 1/2002 |
| WO | 2004030159 | 4/2004 |
| WO | WO-2006058368 | 6/2006 |
| WO | WO-2007070989 | 6/2007 |

* cited by examiner

Section A-A

BRAZE JOIN

CROSS-REFERENCE TO RELATED APPLICATIONS

The present application is a National Stage application of PCT/AU2006/002012 entitled "An Improved Braze Join", filed on Dec. 22, 2006, which claims priority from Australian Provisional Patent Application No. 2005907265 entitled "An Improved Braze Joint", filed on 23 Dec. 2005, which are hereby incorporated by reference.

BACKGROUND

1. Field of Invention

The present invention relates generally to joining two surfaces together using brazing, and more particularly, to an improved braze join.

2. Related Art

Active medical implants are used in many applications in medicine, and include implants for components of the heart, regulated drug delivery systems and cochlear implants. It is essential that these implants are hermetically sealed to prevent the ingress of bodily fluids to the interior of the device as well as contamination of the body from components within the device.

One aspect of hermetic enclosures for active medical implants is electrical connectivity from inside to outside the enclosure, such as connection of the electrical electrode array of a cochlear implant to the electronic circuitry within the hermetic enclosure. A typical construction for this is shown in FIG. 1. Typically, multiple conductive elements 11 are fabricated into a ceramic block to form a feedthrough 10. This may be achieved using processes as described in U.S. Pat. No. 5,046,242 or International Patent Application published as WO2004/030159, which are hereby incorporated by reference herein.

As shown in FIG. 2A, the feedthrough 10 component is then brazed using a braze alloy 12 such as TiCuNi to another component, such as a flange 20. Flange 20 can then be joined (e.g. by laser welding) to the rest of the enclosure (not shown) which is typically formed from a biocompatible metal such as titanium.

FIG. 2B shows a cross section along the line A-A in FIG. 2A, showing flange 20 connected to feedthrough 10 via braze alloy 12.

In practice, a solid ring of braze material or alloy is placed in the gap between feedthrough 10 and flange 20. Brazing is then achieved by heating the assembly to above the melting temperature of the braze alloy but below the melting point of the metal enclosure or ceramic.

One problem, which is common during the typical brazing process, is braze alloy flowing across the surface of the ceramic feedthrough 10 and inadvertently contacting the conducting elements 11. This is typically known as "flooding". Because the braze material 12 is electrically conductive, this braze flooding 13 can cause short circuits between the conductive elements 11 (see FIG. 3) and the resulting assembly has to be discarded.

SUMMARY

According to a one aspect of the present invention, there is provided an assembly of a first component and a second component joined together by a braze material, the assembly comprising: the first component; the second component; a gap defined between a surface of the first component and a surface of the second component; and the braze material in the gap joining the first component and the second component; wherein the braze material has been drawn into the gap by capillary action.

According to another aspect of the present invention, there is provided a component for joining to a second component by a braze material, the component comprising: a surface for joining to a corresponding surface of the second component; and a region on the surface for introducing the braze material between the surface and the corresponding surface.

According to a further aspect of the present invention, there is provided a method of joining a first component and a second component together to form an assembly by brazing, the method comprising: placing a surface of the first component close to a surface of the second component to form a gap therebetween; and introducing a liquid braze material into the gap from at least one of the surface of the first component and the surface of the second component such that the braze material is drawn into the gap by capillary action.

BRIEF DESCRIPTION OF DRAWINGS

The invention will now be described with reference to the following drawings in which.

DETAILED DESCRIPTION

Introduction

Figure 1:
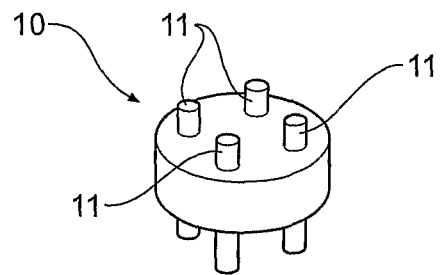
FIG. 1 shows a feedthrough element for use in constructing a braze join of the prior art.
Figure 2A:
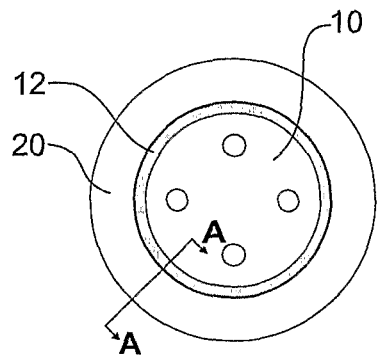
FIG. 2A shows the feedthrough element of FIG. 1 in place in a flange according to one embodiment of the present invention.
Figure 2B:
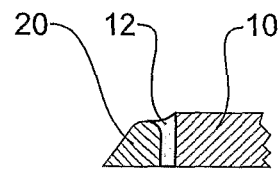
FIG. 2B shows a cross-section along the line A-A of FIG. 2A; according to one embodiment of the present invention

According to one aspect of the present invention, there is provided an assembly of a first component and a second component joined together by a braze material, the assembly comprising: the first component; the second component; a gap defined between a surface of the first component and a surface of the second component; and the braze material in the gap joining the first component and the second component; wherein the braze material has been drawn into the gap by capillary action.

In one form, at least one of the surfaces of the first component and the of the second component has an aperture for introducing the braze material into the gap.

In one form, the aperture is in fluid communication with a recess for receiving the braze material.

In one form, the first component is a flange and the second component is a feedthrough, for use in a medical device.

In another form, the first component is a feedthrough and the second component is a flange, for use in a medical implant.

In one form, the medical device is a cochlear implant.

In one form, the gap is about 3-150 microns wide.

In one form, the gap is about 50-70 microns wide.

According to another aspect of the present invention, there is provided a component for joining to a second component by a braze material, the component comprising: a surface for joining to a corresponding surface of the second component; and a region on the surface for introducing the braze material between the surface and the corresponding surface.

In one form, the region comprises at least one aperture which is in fluid communication with a recess within the component for receiving the braze material.

In one form, the aperture is located substantially in the middle of the surface.

In one form, the region comprises a plurality of apertures.

In another form, the region is a deposit of braze material on the surface.

In one form, the component is a flange for use in a medical device.

In another form, the component is a feedthrough for use in a medical device.

In one form, the medical device is a cochlear implant.

In one form, the deposit is a strip of braze material.

In another form, the deposit is a plurality of strips of braze material.

In yet another form, the deposit is a coating of braze material.

According to a further aspect of the present invention, there is provided a method of joining a first component and a second component together to form an assembly by brazing, the method comprising: placing a surface of the first component close to a surface of the second component to form a gap therebetween; and introducing a liquid braze material into the gap from at least one of the surface of the first component and the surface of the second component such that the braze material is drawn into the gap by capillary action.

In one form, the step of introducing the liquid braze material into the gap comprises placing a supply of braze material into a recess in fluid communication with an aperture in the at least one surface.

In one form, the step of introducing the braze material into the gap further comprises heating the assembly to a temperature at or greater than a melting point of the braze material, and less than a melting point of the assembly.

In one form, the method further comprises cooling the assembly to ambient temperature to allow the heated braze material to solidify.

Description

While embodiments of the present invention is described with reference to a specific application in a cochlear implant, embodiments of the present invention will be understood that the invention is applicable to any braze join where control of the spread of molten braze is desirable (for example to reduce flooding). For example embodiments of the present invention could be applied to metal to metal joins, metal to glass joins, glass to glass joins or ceramic to ceramic joins and it could be used with any braze material including gold alloys, various alloys of titanium including TiCuNi, TiNi, TiCuAg and silver alloys. Embodiments of the present invention are also applicable to other forms of joining one material to another, such as soldering. Furthermore, embodiments of the present invention may be applied to any suitable components such as a flange and a feedthrough as described herein.

Figure 3:
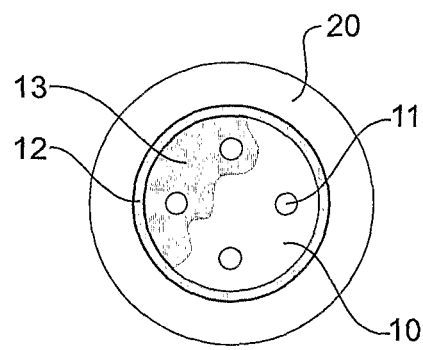
FIG. 3 shows resulting braze flooding from brazing the prior art arrangement of FIGS. 2A and 2B according to one embodiment of the present invention.
Figure 4:
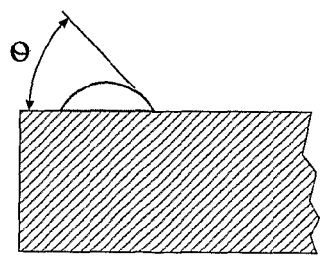
FIG. 4 shows the wetting angle of an amount of liquid braze on a surface according to one embodiment of the present invention.

As a braze material is heated during brazing it changes from a solid to a liquid state. During the liquid state the braze material wets the base material with which it is in contact at a specific wetting angle $\Theta$ (see FIG. 4). The wetting angle depends on a number of factors such as the temperature and the surface properties of the base material. In a typical braze join, to obtain a good braze join it is useful to have good braze material flow. By increasing the brazing temperature, the wetting angle is decreased. The smaller the wetting angle, the better the braze material flow is across the brazing surfaces. Thus in theory, controlling the temperature should ensure controlled flow of the melted braze material across the brazing surface. However the variation of the wetting angle with temperature is non-linear and there are variations in the surface properties of the base material from part to part and even across the surface of a single part, due for example, to localized contamination. Thus surface flow is not easy to control and as a result the braze material's flow may often become unrestrained and flooding occurs as previously described with reference to FIG. 3.

In the braze join design of one aspect of the present invention, the braze flow control is achieved by replacing the free flow of molten braze material across a brazing surface by capillary flow. It has been found that capillary flow is less sensitive to the factors affecting the free surface flow, thus easier to control via controlling the brazing temperature and time of exposure to temperature. The join is designed so that once liquid, the braze material enters the braze join through one or more apertures or access holes.

Figure 5:
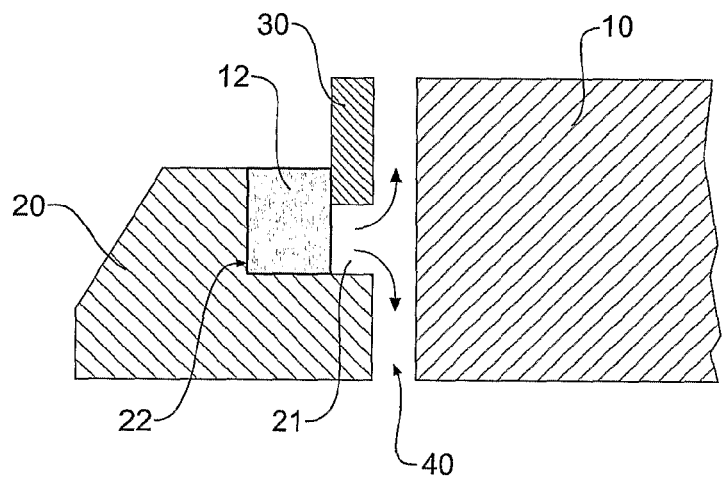
FIG. 5 shows a cross section view of a join according to one embodiment of the present invention.

In one embodiment, an access hole or aperture 21 can be created by means of a secondary collar 30 which fits adjacent to the flange 20 as shown in cross-section in FIG. 5. In this embodiment, a recess 22 is provided in which the braze material 12 is located, and then upon heating, melts and begins to flow through aperture 21 and into the gap 40 defined by or between the surfaces of a first component, made up by in this case, collar 30, flange 20 and second component, provided by, in this case, feedthrough 10.

Figure 6A:
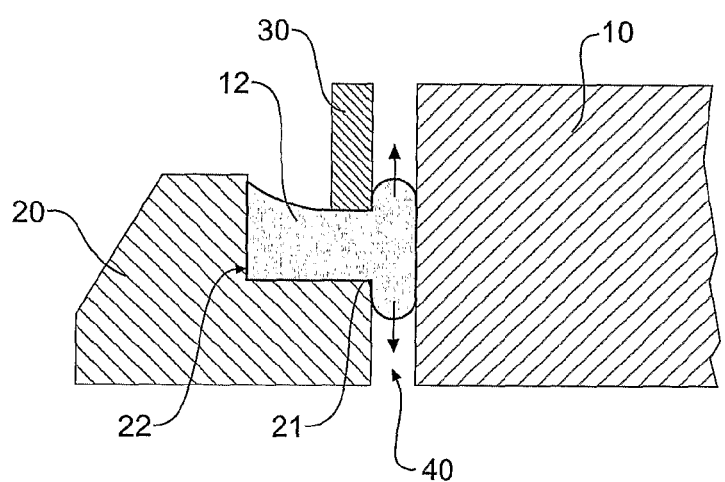
FIG. 6A shows a cross section view of the join of FIG. 5 upon initiating the brazing process according to one embodiment of the present invention.

As the molten braze material flows through aperture 21 and into gap 40, it begins to be drawn into the gap upwards and downwards, by capillary action. This is illustrated in FIG. 6A, which shows braze material 12 flowing through aperture 21 and being drawn into gap 40. The arrows indicate the direction of the capillary forces drawing the braze material 12 upwards and downwards into the gap 40.

Gap 40 is typically 50-70 microns wide but may range from a few microns to 150 microns or more. In particular, the gap may range from about 3-10 microns, 10-20 microns, 20-50 microns, 50-100 microns, 100-125 microns, 125-150 microns, 150-200 microns, or more. The process should work for a braze structure of any size but a typical feedthrough 10 would be about 8 mm diameter and about 1-2 mm thick. The aperture could be between about 10% and about 50% of the feedthrough height. For example, for a 1.6 mm thick feedthrough an aperture of diameter 0.5 mm is suitable. Braze material can be selected to suit the materials being brazed. For brazing an alumina feedthrough to a titanium flange, an alloy of titanium, copper and nickel (TiCuNi) is suitable. The braze temperature is selected to suit the braze material. For a typical TiCuNi braze material such as TiCuNi60, a braze temperature of about 980 C is suitable.

Figure 6B:
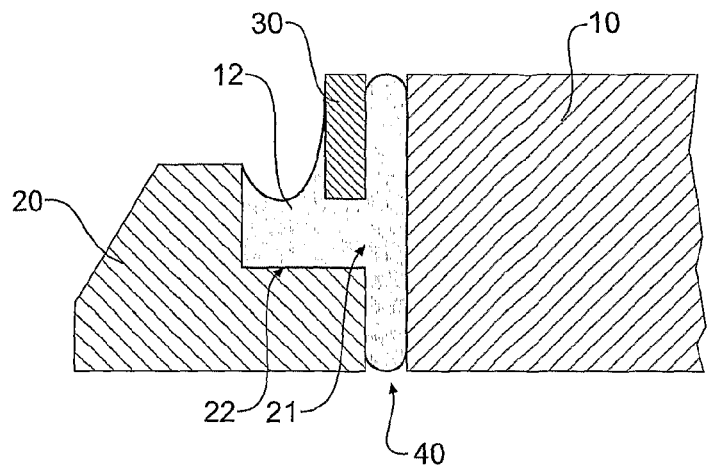
FIG. 6B shows a cross section view of the join of FIG. 6A upon completion of the brazing process according to one embodiment of the present invention.

FIG. 6B shows a later stage of this process with the braze material 12 having reached the limits of the gap 40. Having reached the limits of the gap 40 the capillary forces are no longer present and flow of braze material 12 stops due to surface tension forces of the braze liquid. Any excess braze material 12 will remain in the recess or reservoir 22.

The assembly may then be returned to ambient temperature to allow the braze material to solidify.

As can be seen, the flow of braze material 12 has been able to be controlled much more carefully than when using prior art methods. Accordingly, the risk of flooding has been greatly reduced.

It is also possible to have a pre-prepared component such as a flange which has a surface that is to be joined to another component, where at least a portion of the surface is coated with the braze material. The braze material may be painted on or otherwise applied, or may be deposited within a small recess or depression in the surface.

As the component is heated, the braze material will melt and be drawn into the gap by capillary action as previously described.

Alternatively, the braze material could be deposited or painted onto the surface in layers. For example TiCuNi would be formed by a layer of Ti, a layer of CuNi alloy and another layer of Ti. A mask could be used so that the braze is only deposited where required.

Figure 7A:
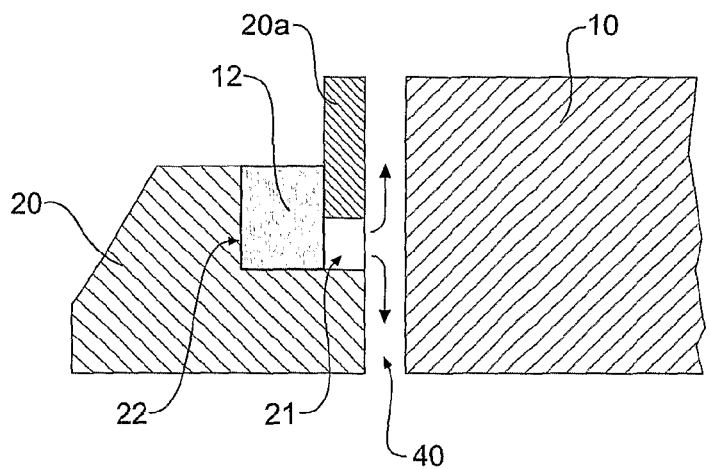
FIG. 7A shows a cross-sectional view of a join according to a second embodiment of the present invention.

In another embodiment, the flange 20 itself can be formed with one or more holes 21, which may be circular or otherwise, as an integral part. This embodiment is shown in FIG. 7A, where collar 30 from the previous embodiment described above is provided by a part 20a of the flange 20. In all other aspects, this embodiment is essentially the same as that shown in FIGS. 5, 6A and 6B.

The liquid braze 12 flows under capillary action from recess 22 into the gap 40 between the two surfaces to be joined, via aperture 21. In this embodiment capillary flow will occur to left and right as well as upwards and downwards resulting in a complete braze join. Control of the braze parameters, particularly temperature and time, ensure good control of capillary flow of the braze material in the join, hence the braze material does not flow beyond the braze join region and flooding is prevented. This level of control can be achieved for example using an infrared brazing oven as would be understood by the person skilled in the art.

For a TiCuNi braze material, suitable parameters would be to have a controlled ramp up to 980° C. with a hold at 980° C. for 30 seconds and then a ramp down to room temperature. The controlled ramp up may include one or more hold temperatures to allow parts to reach thermal equilibrium before ramping to the final hold temperature.

Figure 7B:
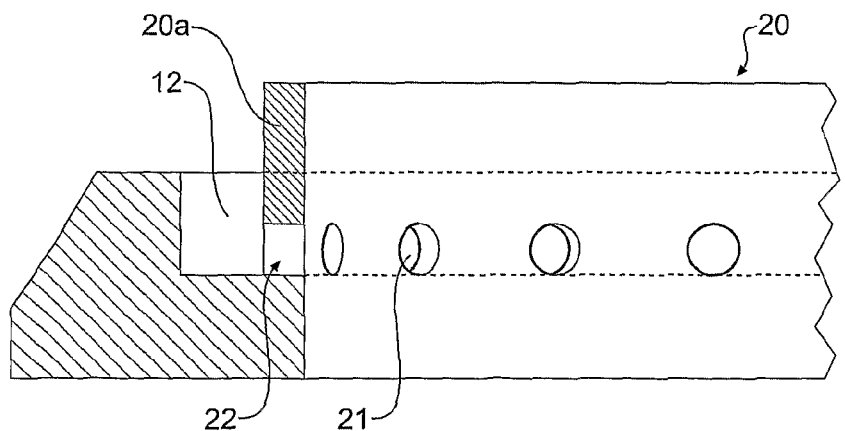
FIG. 7B shows a partial cross-sectional side view of the flange of FIG. 7A according to one embodiment of the present invention.

FIG. 7B shows a side view and partial cross-sectional view of a flange 20 constructed according to this embodiment, with recess or reservoir 22 for receiving braze material (not shown), and a series of apertures 21 extending along the flange portion 20a to allow access to the join (not shown).

Figure 7C:
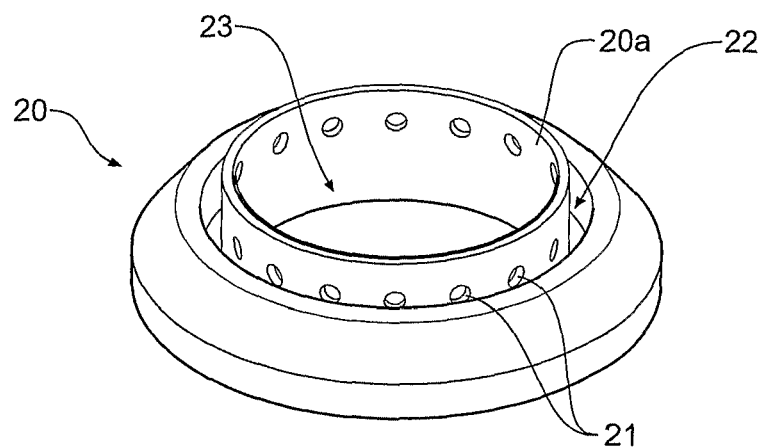
FIG. 7C shows a perspective view of the flange of FIG. 7B according to one embodiment of the present invention.

FIG. 7C is a perspective view of a flange 20 designed according to this embodiment. Shown there is recess 22 in which braze material (not shown) may be placed, such that upon heating, the braze material flows into apertures 21 and is drawn into the gap or join (not shown) which exists when a feed through (not shown) is placed within the circular aperture 23 of the flange 20.

In an exemplary practical application using the braze join according to one aspect of the present invention, the join could be constructed as follows. Firstly, the ceramic feedthrough may be fabricated using the process described in PCT/AU2003/001288 (WO2004/030159), herein incorporated by reference herein.

A titanium flange may then be created by machining, to provide multiple holes around the circumference (see for example FIG. 7C). The internal diameter of the flange should be larger than the external circumference of the ceramic feedthrough. For convenient braze application the flange can also contain a braze reservoir as previously described.

An active braze such as TiCuNi is applied into the reservoir either by using rings of TiCuNi foil such as that provided by companies such as WESGO Ceramics, a Division of Morgan Advanced Ceramics, Inc in California, USA or by dispensing TiCuNi paste such as that provided by Lucas-Milhaupt, Inc. a Wisconsin company in the USA. The assembly is then heated in an infrared brazing oven to a temperature above the liquid temperature of the braze material and held there for a sufficient time to ensure good capillary flow of the braze material into the join to be brazed.

In the present example, a typical temperature to which the assembly is heated is 980° C. for one minute.

Figure 8:
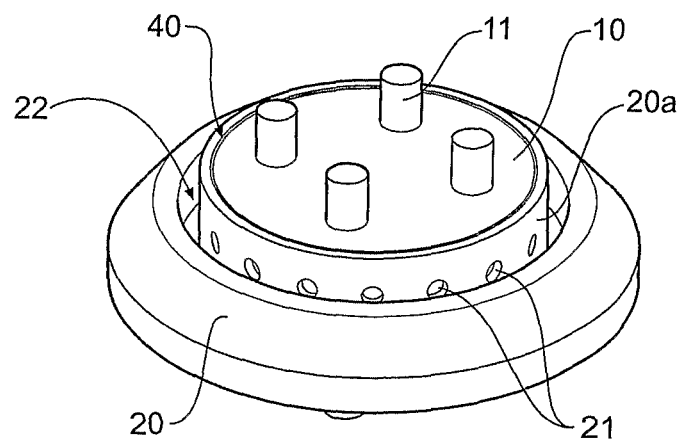
FIG. 8 shows the flange of FIG. 7C brazed to the feedthrough of FIG. 1 according to one embodiment of the present invention.

An exemplary join formed by the above process is shown in FIG. 8, which shows flange 20 joined to ceramic feedthrough 10 supporting conductors 11. The join is created by brazing by having placed braze material in the recess or reservoir 22 and heating the braze material as described above so that the braze material passes through apertures 21 to be drawn by capillary action into the gap 40 to create the join.

It will be appreciated that in some assemblies it may be difficult or undesirable to fabricate parts with the braze access holes 21 shown in FIGS. 7 and 8. In an alternative embodiment, braze access is achieved by means of slots 24 (see FIG. 9). The slots will be narrow enough such that the primary transport mechanism of braze material around the join is via capillary action, and surface tension in the braze liquid at the gap edges is not significantly affected, thus could still contain potential free-flow.

Slot widths of 0.5 mm are suitable for feedthrough assemblies having dimensions as described previously.

According to a further embodiment of the present invention, it is possible to fabricate the join such that the braze reservoir is within the join such that flow from the reservoir is still via capillary action.

Figure 10:
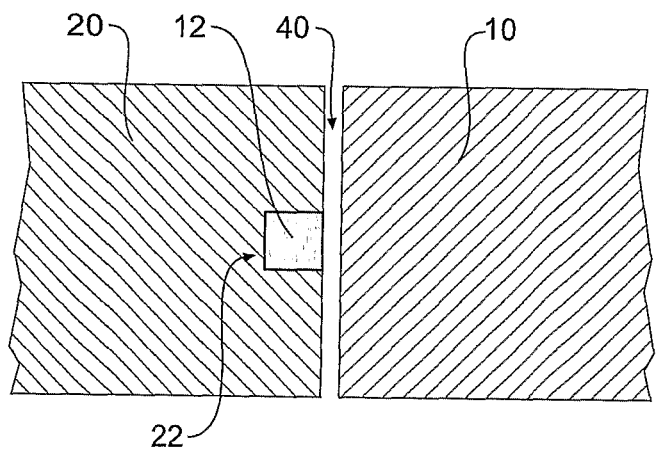
FIG. 10 shows a cross-sectional view of a braze join with a braze reservoir within the join according to one embodiment of the present invention.

In this embodiment (see FIG. 10), a recess or reservoir 22 is formed within an inner surface of flange 20, and a supply of braze material 12, for example in solid or paste form, is inserted in the recess. After assembly of the flange and feedthrough 10, the assembly is heated as described above and the braze material 12 in recess 22 melts and is drawn out of recess 22 into gap 40 by capillary action, to form the braze join.

Figure 11:
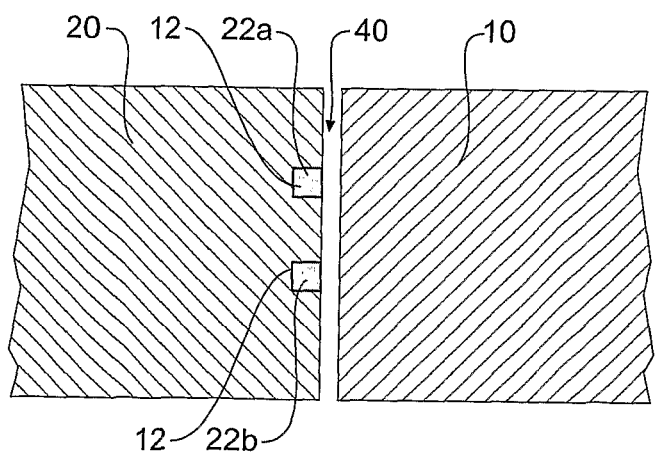
FIG. 11 shows a cross-sectional view of a braze join with two braze reservoirs within the join according to one embodiment of the present invention.

In practice, the flange 20 may have formed within it a series of recesses 22 around its inner circumference so as to provide an even distribution of braze material to form a strong join. As shown in FIG. 11, it is also possible to provide two rings of smaller recesses at different levels to provide even greater control of flow of braze material.

It will be understood that the above has been described with reference to particular embodiments and that many variations and modifications may be made within the scope of the present invention.

Figure 12:
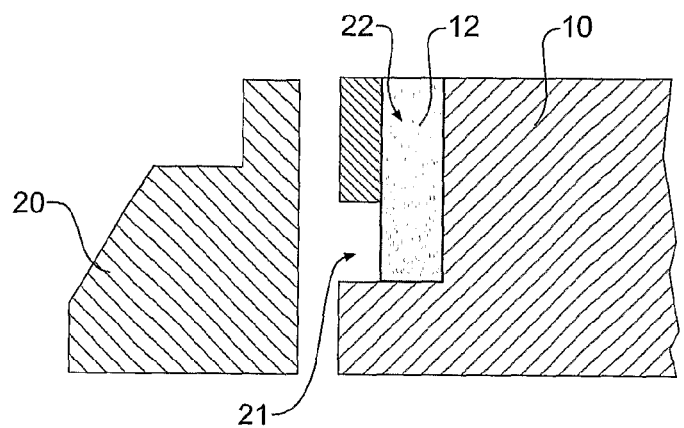
FIG. 12 shows an alternative form of the arrangement of FIG. 5 according to one embodiment of the present invention.

For example, the aperture(s) and/or recess(es) may be provided in the other component (in the above examples, in the feedthrough and not in the flange). FIG. 12 shows the arrangement of FIG. 5 but with the aperture 21 and recess 22 provided in feedthrough 10.

Figure 9:
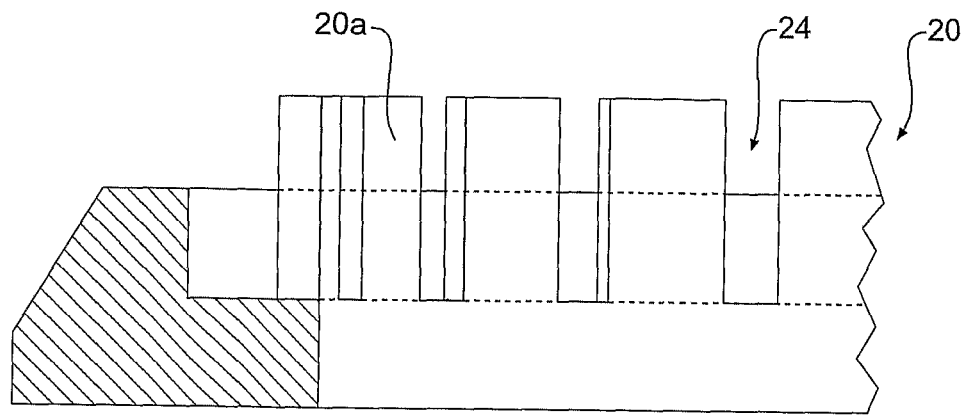
FIG. 9 shows a partial cross-sectional side view of an alternative form of the flange of FIG. 7B according to one embodiment of the present invention.
Figure 13A:
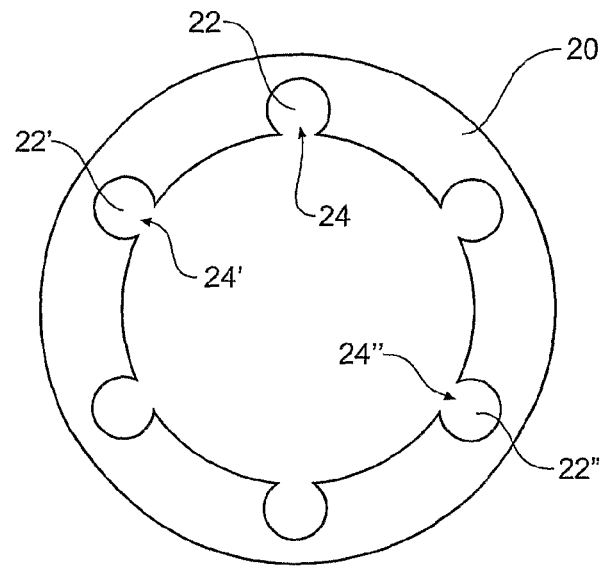
FIGS. 13A and 13B show an alternative of the arrangement of FIG. 9 according to one embodiment of the present invention.

In a further modification to the arrangement shown in FIG. 9, flange 20 may have more than one, or all of its slots 24 fed by its own reservoir of braze material. FIG. 13A shows flange 20 with a plurality of slots 24, 24', 24" etc, with corresponding recesses or reservoirs 22, 22' and 22" etc.

Figure 13B:
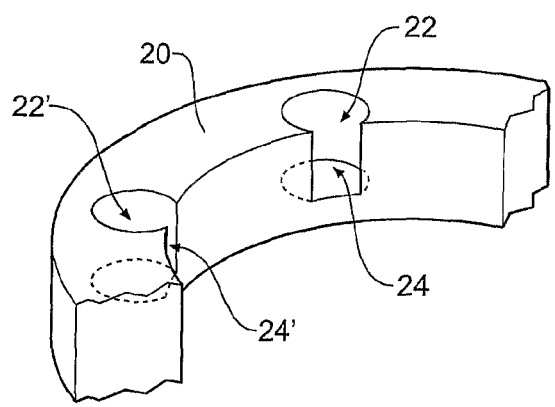

FIG. 13B shows a partial perspective view of FIG. 13A, showing the configuration of slots 24, 24' and corresponding recesses or reservoirs 22, 22'.

This arrangement could be equally applied to the arrangement in which slots 24 are apertures 21 as in the arrangement of FIG. 7C for example.

Figure 14A:
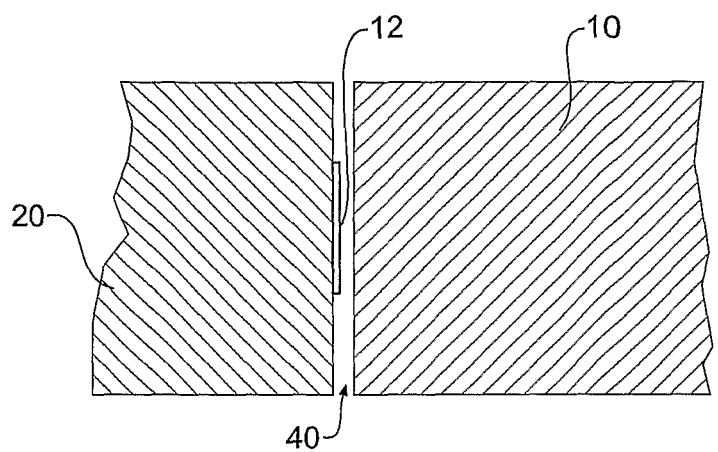
FIG. 14A shows an application in which braze material is provided as a strip according to one embodiment of the present invention.

In a further modification and as briefly described above, braze material 12 may be introduced into gap 40 as a deposit of braze material, in the form of a strip or coating of braze material on an inside surface. FIG. 14A shows this application, with flange 20 and feedthrough 10 defining gap 40 therebetween. In this example, the braze material is provided by a strip 12 of the material as previously described. Alternatively, the material supply could be painted on as a coating, again as previously described.

Figure 14B:
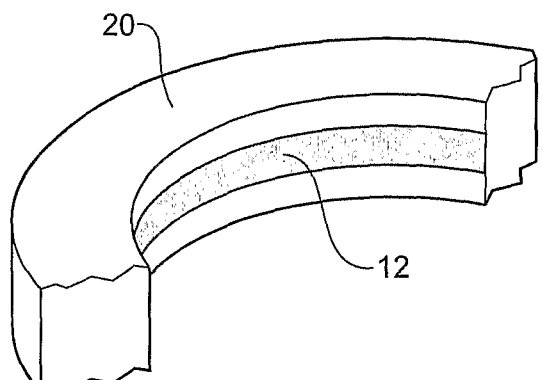
FIG. 14B shows the application of FIG. 14A to the arrangement of FIG. 13B according to one embodiment of the present invention.
Figure 14C:
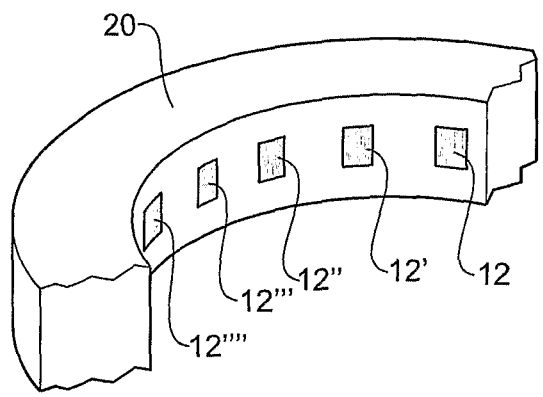
FIG. 14C shows an alternative to the arrangement of FIG. 14B according to one embodiment of the present invention.

In FIG. 14B, this application is shown in use as an alternative to that used in the arrangement of FIG. 13B. In this application, recesses 22 and slots 24 are replaced by a strip 12 of the braze material. In one form, strip 12 can extend entirely around the inner circumference of flange 20. In another form, the braze material may be provided by a plurality of discrete strips or patches 12, 12', 12", 12''', 12'''' etc.

Upon heating, as previously described, the braze material melts and is spread across the inner surface of flange 20 into gap 40 to form the join between flange 20 and feedthrough 10.

Of course, it will also be understood that strips 12 can be applied to the inner surface of feedthrough 10 and not on the inner surface of flange 20, or indeed on both.

Further variations and modifications may also include for example, the component (such as the flange) to be joined to another component by brazing could be made from a porous material which could be infused with a braze material. In this case, the material could be porous on the side but not top and bottom otherwise the braze would flow through the pores onto unwanted surfaces. This could be achieved using a laminated material where the centre is made from a porous material and the top and bottom are non porous. Technology for laminating ceramic exists for example in the hybrid electronics industry and for metals is used widely and may be achieved by co-rolling. The braze material could be introduced into the porous component before it is laminated.

As previously stated, it will also be understood that the various aspects of the present invention described herein may be applied to applications other than medical devices, where a first component and a second component are required to be joined together by a braze or a welding or soldering method. It will be understood that these applications are also encompassed by the various aspects described herein.

It will also be understood that throughout this specification, unless the context requires otherwise, the words 'comprise' and 'include' and variations such as 'comprising' and 'including' will be understood to imply the inclusion of a stated integer or group of integers but not the exclusion of any other integer or group of integers.

The reference to any prior art in this specification is not, and should not be taken as, an acknowledgement or any form of suggestion that such prior art forms part of the common general knowledge.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

The invention claimed is:

1. A method of joining a first component and a second component together to form an assembly by brazing, the method comprising:
    placing a surface of the first component proximate to a surface of the second component to form a gap therebetween;
    introducing a liquid braze material into the gap from at least one of the surface of the first component or the surface of the second component such that the braze material is drawn into the gap by capillary action; and
    placing a supply of braze material into a recess of at least one of the first and second components, the recess being in fluid communication with a plurality of apertures in the at least one surface.

2. The method as claimed in claim 1, wherein the step of introducing the braze material into the gap further comprises heating the assembly to a temperature at or greater than a melting point of the braze material, and less than a melting point of the first and second component, and drawing at least some of the liquid braze material from the recess through the plurality of apertures and into the gap by capillary action.

3. The method as claimed in claim 2, wherein the method further comprises the step of placing the supply of braze material into the recess prior to placing the surface of the first component proximate to the surface of the second component to form the gap therebetween.

4. The method as claimed in claim 1, wherein the braze material is confined within the assembly when in the liquid form.

5. The method of claim 1, the method further comprising:
    allowing the liquid braze material to solidify such that a capillary meniscus extends from the surface of the first component to the surface of the second component.

6. The method of claim 1, wherein:
    the first component is a flange of a medical device implant and the second component is a feedthrough of a medical device implant.

7. The assembly as claimed in claim 6, wherein the medical device implant is a cochlear implant.

8. The method of claim 6, wherein the feedthrough is a connection providing electrical connectivity from inside to outside of a hermetic enclosure of a cochlear implant.

9. The method of claim 6, wherein the recess is at least partially formed by a secondary collar adjacent the flange or the feedthrough.

10. The method of claim 1, wherein the gap is about 3-150 microns in width.

11. The method of claim 1, wherein the aperture is located substantially in the middle of the surface.

12. The method of claim 1, wherein the plurality of apertures comprise at least one hole.

13. The method of claim 1, wherein the plurality of apertures comprise at least one slot.

14. The method of claim 1, wherein one of the first component and the second component is titanium, the other of the first component and the second component is aluminum, and the braze material is an alloy of titanium, copper and nickel.

15. A method of joining a first component and a second component together to form an assembly by brazing, the method comprising:
    placing a surface of the first component proximate to a surface of the second component to form a gap therebetween;
    introducing a liquid braze material into the gap from at least one of the surface of the first component or the surface of the second component such that the braze material is drawn into the gap by capillary action; and
    placing a supply of braze material into a recess of at least one of the first and second components, the recess being in fluid communication with an aperture in the at least one surface,
    wherein the recess is at least partially formed by a secondary collar adjacent the first component or the second component.

16. The method as claimed in claim 15, wherein the step of introducing the braze material into the gap further comprises heating the assembly to a temperature at or greater than a melting point of the braze material, and less than a melting point of the first and second component, and drawing at least some of the liquid braze material from the recess through the aperture and into the gap by capillary action.

17. The method as claimed in claim 16, wherein the method further comprises the step of placing the supply of braze material into the recess prior to placing the surface of the first component proximate to the surface of the second component to form the gap therebetween.

18. The method as claimed in claim 15, wherein the braze material is confined within the assembly when in the liquid form.

19. The method of claim 15, the method further comprising:
    allowing the liquid braze material to solidify such that a capillary meniscus extends from the surface of the first component to the surface of the second component.

20. The method of claim 15, wherein:
    the first component is a flange of a medical device implant and the second component is a feedthrough of a medical device implant.

21. The assembly as claimed in claim 20, wherein the medical device implant is a cochlear implant.

22. The method of claim 20, wherein the feedthrough is a connection providing electrical connectivity from inside to outside of a hermetic enclosure of a cochlear implant.

23. The method of claim 15, wherein the gap is about 3-150 microns in width.

24. The method of claim 15, wherein the aperture is located substantially in the middle of the surface.

25. The method of claim 15, wherein the recess is in communication with a plurality of apertures.

26. The method of claim 15, wherein the aperture comprises a hole.

27. The method of claim 15, wherein the aperture comprises a slot.

28. The method of claim 15, wherein one of the first component and the second component is titanium, the other of the first component and the second component is aluminum, and the braze material is an alloy of titanium, copper and nickel.

* * * * *